United States Patent
Lee et al.

(10) Patent No.: US 10,058,266 B2
(45) Date of Patent: Aug. 28, 2018

(54) SIGNAL PROCESS SYSTEM AND METHOD FOR THE SAME AND BIOLOGICAL RESISTANCE DETECTION DEVICE AND ELEMENT

(71) Applicant: National Cheng Kung University, Tainan (TW)

(72) Inventors: Shuenn-Yuh Lee, Tainan (TW); Tsung-Han Tsai, New Taipei (TW)

(73) Assignee: NATIONAL CHENG KUNG UNIVERSITY, Tainan (TW)

(*) Notice: Subject to any disclaimer, the term of this patent is extended or adjusted under 35 U.S.C. 154(b) by 637 days.

(21) Appl. No.: 14/644,469

(22) Filed: Mar. 11, 2015

(65) Prior Publication Data
US 2015/0362448 A1  Dec. 17, 2015

(30) Foreign Application Priority Data
Jun. 11, 2014 (TW) .............................. 103120260 A

(51) Int. Cl.
| | | |
|---|---|---|
| *G01N 27/00* | (2006.01) | |
| *A61B 5/053* | (2006.01) | |
| *A61B 5/00* | (2006.01) | |

(52) U.S. Cl.
CPC ............ *A61B 5/053* (2013.01); *A61B 5/0537* (2013.01); *A61B 5/7225* (2013.01)

(58) Field of Classification Search
CPC ...... G01N 27/00; A61B 5/053; A61B 5/0537; A61B 5/7225
USPC ....... 422/50, 68.1, 82.01, 82.02; 436/43, 63, 436/149, 806; 600/300, 372, 377, 384; 702/19, 30, 31, 32, 57
See application file for complete search history.

(56) References Cited

U.S. PATENT DOCUMENTS 5,372,141 A * 12/1994 Gallup ................ A61B 5/0002
                                                600/547
5,503,157 A *  4/1996 Sramek ............... A61B 5/0535
                                                600/506

(Continued)

FOREIGN PATENT DOCUMENTS

| CN | 202121568 U | 1/2012 |
| CN | 2033379116 U | 1/2014 |

(Continued)

OTHER PUBLICATIONS

Official action issued by SIPO (State Intellectual Property Office of the P.R.C.) dated Aug. 7, 2017.

(Continued)

*Primary Examiner* — Brian J Sines
(74) *Attorney, Agent, or Firm* — Chun-Ming Shih

(57) ABSTRACT

A signal process system and the method for the same and a biological resistance detection device and element used to perform corresponding signal process for sensory signal sensed by a sensor, wherein a minor AC electrical signal is injected into a biological tissue to be measured in order to sense the sensory signal of the biological tissue to be measured by means of the principle of Ohm's Law. Moreover, the sensory signal may be processed to restore a biological property of the measured biological tissue and to create an equivalent circuit parameter model representative of the biological property.

6 Claims, 3 Drawing Sheets

(56) References Cited

U.S. PATENT DOCUMENTS

2013/0006136 A1* 1/2013 Biancolillo .......... A61B 5/0535
600/547
2017/0354345 A1* 12/2017 Biancolillo .......... G01N 27/028

FOREIGN PATENT DOCUMENTS

WO    WO2013/030425 A1    3/2013
WO    WO2013030425 A1    3/2013

OTHER PUBLICATIONS

Official action issue by SIPO (State Intellectual Property Office of the P.R.C.) dated Jan. 19, 2018.

* cited by examiner

SIGNAL PROCESS SYSTEM AND METHOD FOR THE SAME AND BIOLOGICAL RESISTANCE DETECTION DEVICE AND ELEMENT

CROSS-REFERENCE TO RELATED APPLICATIONS

This application claims the priority of Republic of China Patent Application No. 103120260 filed on Jun. 11, 2014, in the State Intellectual Property Office of the R.O.C., the disclosure of which is incorporated herein by reference.

BACKGROUND OF THE INVENTION

Field of the Invention

A signal process technology is related, particularly to a signal process system dividing a biological impedance information into two portions, gain and phase, for detection by using resistive property and capacitive property of a biological tissue to be measured, and the method for the same, and a biological impedance detection device and element.

Descriptions of the Related Art

Biological impedance technology is an important technology in clinical medicine and biomedicine fields for nature determination or quantification of characteristic behaviors of various biological tissues to observe differences of different biological tissues from the characteristic behaviors essentially on the basis of existing electrical properties and frequency response properties of biological tissues themselves.

In early stage, the biological impedance technology is applied to fitness assessment of athletes, weight reduction, body fat meter and nutriology. In recent stage, it is mainly applied to monitor changes of status of blood, body fluid and different body tissues, for example, heart failure treatment, breath parameters measurement, cell property detection, nutrition status of patients, cardio-pulmonary function evaluation and biological impedance image. In recent years, the biological impedance technology is further applied to cancer detection for the comparison between normal cells and cancer cells as important references to determine whether or not cancer cells grow after surgery and to determine cancer recurrence or metastasis.

Compared to other detection methods (for example, isotope method, radioactive potassium tracking, ultrasonic wave, MRI (Magnetic Resonance Imaging) and CT (Computer Tomography) etc., the biological impedance is advantageous of easy operation, rapid analysis, high precision, and non-intrusion etc. Therefore, the biological impedance technology is an important development direction for biomedicine or clinical medicine now.

As mentioned above, the biological impedance technology can be applied to cancer detection. Particularly, for cancer postoperative patients, recurrent tumors still appear in original tumor sites for a certain proportion of patients as time goes by even though the clinical syndromes used to disappear through treatment after tumor cells are removed via surgery. Therefore, recurrence or transfer have to be followed up and monitored regularly either after surgery or treatment, and it is one of the current main directions to research how to implement such technology in implantable or portable biomedical electronic detection systems.

For previously various biological impedance technologies, the Wheatstone Bridge impedance detection technology proposed in the early years of the 19th century was used to measure impedance value of unknown impedance. In this technology, a galvanometer was placed in the middle to detect flow of current. As the reading from the galvanometer is zero, the potentials at two ends of the galvanometer are balanced and the impedance value of the object to be measured is known. This technology was advantageous of high resolution, accuracy and easy operation of device etc. However, more time was necessary to adjust balance of the bridge in measurement, such that it is not suitable for biological impedance that would change with time. Moreover, this technology itself consumed higher power and more hardware space was needed for implementation. Hence, this technology was not applicable to implantable or portable biological impedance detection system.

The more popular FRA (Frequency Response Analysis) technology used now utilizes PSD (Phase-Sensitive Detection), through which the information of both real part and imaginary part of impedance can be obtained directly. Principally, the original detection signal is used to perform demodulation with in-phase signal and quadrature-phase signal, respectively, to obtain real part and imaginary part signals of the impedance. This detection technology can provide higher accuracy and wider applicable frequency range, and achieve higher impedance detection speed compared to aforementioned Wheatstone Bridge technology. Moreover, it is capable of continuous detection insensitive to the change of the impedance of the object to be measured, which changes with time. Furthermore, its output signal is just the real part and imaginary part of the impedance of the object to be measured, such that it can restore real impedance via simple calculation.

However, the aforementioned biological impedance technology using PSD obtains the real part and imaginary part of the impedance from demodulation by two reference clock signals with different phases, so that an additional circuit is necessary to generate two reference signals, in-phase and quadrature-phase. The demodulation output result depends directly on the accuracy and the match of the two reference signals, which have different phases. Therefore, it is very important to generate reference signals which are accurate and have different phases. This would increase the complexity in implementing the circuit and increase the overall power consumption of the system. More hardware implementations are necessary for it to be an implantable or portable device. As a result, it is not applicable to implantable or portable device.

From above descriptions, the implantable or portable biological impedance detection system and the method for implementing the same are the technical subjects those skilled in the art are eager to explore currently.

SUMMARY OF THE INVENTION

The invention provides a signal process system and the method for the same and a biological impedance detection device and element capable of performing monitoring with the change of biological impedance, reduction of hardware need and power consumption, and reduction of implementation complexity.

To achieve above object and other object, the invention provides a signal process method to perform a corresponding signal process for a sensory signal sensed by a sensor for obtaining a sensory result from a biological tissue to be measured, including the following process steps: injecting a minor AC electrical signal to pass through said biological tissue to be measured for said sensor to sense the sensory signal from said biological tissue to be measured by the principle of Ohm's Law; and processing said sensory signal to output a first digital output signal related to a signal strength, and processing both of said minor AC electrical signal and said sensory signal to output a second digital output signal related to a phase; thereby, said first digital output signal and said second digital output signal are utilized to restore a physiological property of said biological tissue to be measured; in addition, the two signals may be utilized to restore an equivalent circuit parameter model representative of the physiological property of said biological tissue to be measured in order to be provided for researches in, for example, clinical medicine or biomedicine engineering fields.

The invention further provides a signal process system used to perform a corresponding signal process for a sensory signal sensed by a sensor to obtain a sensory result of a biological tissue to be measured, said biological tissue generating the sensory signal for sensing performed by said sensor according to a stimulus signal, including: a gain detection module for receiving said sensory signal to process said sensory signal and output a first digital output signal related to a signal strength; and a phase detection module for receiving said stimulus signal to process said stimulus signal and said sensory signal and output a second digital output signal related to a phase, such that said first digital output signal and said second digital output signal are used to restore a physiological property of the biological tissue to be measured and create an equivalent circuit parameter model representative of said physiological property.

Said gain detection module of said signal process system of the invention includes at least: a signal amplifier for amplifying said sensory signal to generate an amplified signal; a first square wave generator for converting said sensory signal into a first square wave signal; a signal mixer, which mixes said amplified signal and said first square wave signal to generate a mixed output signal; a filter for filtering said mixed output signal to filter out undesired frequency component from said mixed output signal for generation of a filtered output signal with a selected frequency; and an analog-to-digit converter for converting said filtered output signal with the selected frequency into said first digital output signal.

Furthermore, said phase detection module of said signal process system of the invention includes at least: a second square wave generator for converting said stimulus signal into a second square wave signal; and a time-to-digit converter for quantifying a time difference between said first square wave signal and said second square wave signal to output said second digital output signal.

The invention further provides a biological impedance detection device for a near-end device to perform signal process using said first digital output signal and said second digital output signal, said biological impedance detection device including: a micro stimulus generator for providing said stimulus signal to said biological tissue to be measured; a biological impedance detection element for building in said gain detection module and said phase detection module; a wireless transceiving end for receiving a signal from said near-end device or transmitting a local signal to said near-end device; a system controller used to control said micro stimulus generator and said biological impedance detection element for said near-end device to restore a impedance information of said biological tissue to be measured from said first digital output signal and said second digital output signal, and to create the equivalent circuit parameter model representative of said impedance information; a demodulator for demodulating a signal from said near-end device; a modulator for modulating the transmitted local signal; and a wireless energy transfer interface for providing electrical energy to provide the electrical energy necessary for said demodulator, said system controller, said micro stimulus generator, said modulator and said biological impedance detection element.

Furthermore, said biological impedance detection device of the invention is implanted into said biological tissue to be measured in a chip form. Otherwise, for said biological impedance detection device of the invention, the equivalent circuit parameter model representative of said impedance information is formed by connecting a base resistor and a set of parallel connected resistor and capacitor in series.

The signal process system and the method for the same and the biological impedance detection device and element of the invention may be applied to measure signal level difference and phase difference of different signals for further application in detection of biological impedance. In biological impedance detection, impedance information of a biological tissue may be derived by measuring a frequency response of said biological tissue to a stimulus signal (including signal gain ($|Z|$) and phase ($\Phi$)), and said impedance information may be further utilized to be reference for syndrome diagnosis. Also, the signal process system and the method for the same and the biological impedance detection device and element of the invention have good integrated characteristic capable of solving conventional problems, including excessive hardware need of impedance detection device, excessive power consumption and complex design etc.

DETAILED DESCRIPTION OF THE PREFERRED EMBODIMENT

Figure 1:
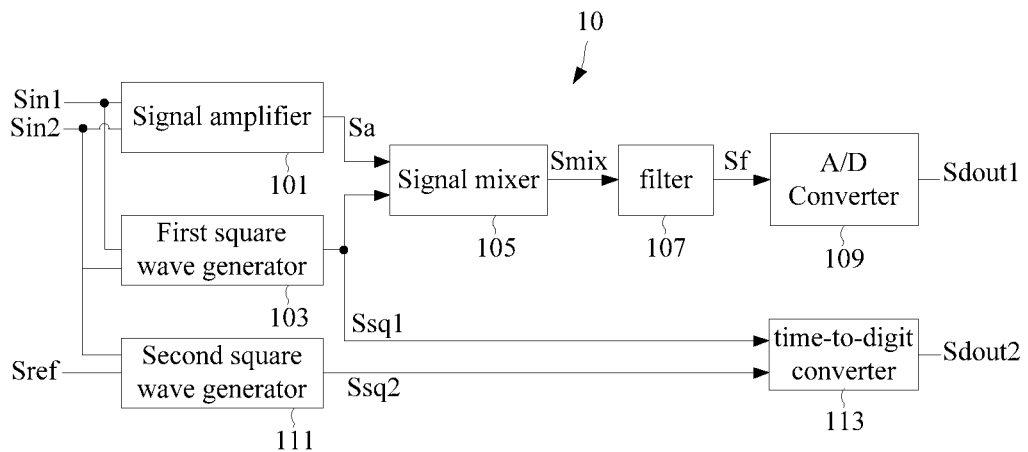
FIG. 1 is a block diagram of one example of the signal process system according to the invention.

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

It is noted that the signals mentioned in examples of the invention may be voltage, current or charge signals according to different implementation approaches.

FIG. 1 shows a block diagram of one example according to a signal process system 10 of the invention. A corresponding signal process is performed for a sensory signal sensed by a sensor to further obtain a physiological property of a biological tissue to be measured. However, the signal process performed by the signal process system of the invention is for said sensory signal by dividing said sensory signal into two parts, gain (|Z|) and phase (Φ) for detection, in order to restore the complete physiological property of the biological tissue to be measured and restore a equivalent circuit parameter model representative of said physiological property, but not limited thereto. For example, a biological impedance is detected, and before detection, a minor AC electrical signal may be injected to pass through said biological tissue to be measured for detection of said biological tissue to be measured by using said minor AC electrical signal as a stimulus signal, in addition, the principle of Ohm's Law is used for said sensor to sense the sensory signal of said biological tissue to be measured. It is further noted that the aforementioned minor AC electrical signal may be, for example, current, voltage or charge.

Based on the detection of both gain (|Z|) and phase (Φ), the signal process system 10 of the invention includes at least: a gain detection module and a phase detection module. Said gain detection module is used to receive the sensory signal sensed by said sensor for said biological tissue to be measured in order to process said sensory signal and output a first digital output signal related to a signal strength, while said phase detection module is used to receive said stimulus signal in order to process said stimulus signal and said sensory signal for outputting a second digital output signal related to the phase. Thereby, said first digital output signal and said second digital output signal may be utilized to restore said physiological property of the biological tissue to be measured, and to create the equivalent circuit parameter model representative of said physiological property.

Said gain detection module includes at least: a signal amplifier 101, a first square wave generator 103, a signal mixer 105, a filter 107 and an analog-to-digit converter 109; while said phase detection module includes at least: a second square wave generator 111 and a time-to-digit converter 113.

Said signal amplifier 101 is used to amplify said sensory signal to generate an amplified signal Sa for receiving. As shown in FIG. 1, a minor stimulus signal is injected into the biological tissue to be measured. Said signal amplifier 101 is used to retrieve a first input signal Sin1 and a second input signal Sin2 generated by flowing through said biological tissue to be measured, so that an amplified signal Sa is obtained after amplification. For example, said signal amplifier 101 may be a voltage (V/V), current (I/I), transconductance (I/V) or transimpedance (V/I) amplifier, and said signal amplifier 101 may have an adjustable gain, which is used to amplify said sensory signal. Moreover, said adjustable gain may be adjusted or calibrated according to design.

Said first square wave generator 103 is used to convert said sensory signal into a first square wave signal. As shown in FIG. 1, for example, signal level (voltage/current) magnitudes of said first input signal Sin1 and said second input signal Sin2 are determined or compared. A first square wave signal Ssq1 is generated according to determination or comparison result. If said first input signal Sin1 is larger than said second input signal Sin2, then said first square wave signal Ssq1 may be a positive saturated output signal (for example, an output signal having a high logic level (logic 1)); if said first input signal Sin1 is smaller than said second input signal Sin2, then said first square wave signal is a negative saturated output signal (for example, an output signal having a low logic level (logic 0)). For example, said first square wave generator 103 may be any transistor amplifier or comparator. As a signal level (voltage/current) difference between the two input signals is larger than a predetermined threshold, an output signal generating logic 1 or 0 (digital circuit) is generated or a saturated output signal (analog circuit) is generated.

Said signal mixer 105 mixes said amplified signal Sa and said first square wave signal Ssq1 to generate a mixed output signal Smix. For example, said signal mixer 105 may be a mixer or frequency mixer used to perform mixing or frequency mixing for said amplified signal Sa and said first square wave signal Ssq1 with the same or different frequency components.

Said filter 107 filters said mixed output signal Smix for filtering out undesired frequency components from said mixed output signal Smix to generate a filtered output signal Sf with a selected frequency. For example, depending on design, said filter 107 may be any type of filter, such as low pass filter, high pass filter, band pass filter, notch filter or the combination thereof.

Said analog-to-digit converter 109 is used to convert said filtered output signal Sf with the selected frequency into a first digital output signal Sdout1 related to a signal strength. For example, depending on design, said analog-to-digit converter 109 may be any type of analog-to-digit converter.

For the phase detection module used for detection of phase (Φ), said second square wave generator 111 is used to convert said stimulus signal into a second square wave signal Ssq2. In FIG. 1, signal level magnitudes of said second input signal Sin2 and a reference signal (voltage/current) Sref are determined and compared, the result therefrom is used to generate a second square wave signal Ssq2. If said second input signal Sin2 is larger than said reference signal Sref, then said second square wave signal Ssq2 is a positive saturated output signal (for example, logic 1 output signal); if said second input signal Sin2 is smaller than said reference signal Sref, then said second square wave signal Ssq2 is a negative saturated output signal (for example, logic 0 output signal).

Said time-to-digit converter 113 is used to quantify the time difference between the first square wave signal Ssq1 and the second square wave signal Ssq2, and output a second digital output signal related to a phase. Referred to FIG. 1, for example, the time difference between a rising edge of said first square wave signal Ssq1 and a rising edge of said second square wave signal Ssq2 may be converted into a second digital output signal Sdout2, or the time difference between a falling edge of said first square wave signal Ssq1 and a falling edge of said second square wave signal Ssq2 may be converted into the second digital output signal Sdout2 related to a phase. In other words, said time-to-digit converter 113 may convert a time difference between rising or falling edges of different input signals into a digital output signal. For example, depending on design, said time-to-digit converter 113 may also be implemented using simple logic gate combinational circuits or timing circuits.

Figure 2:
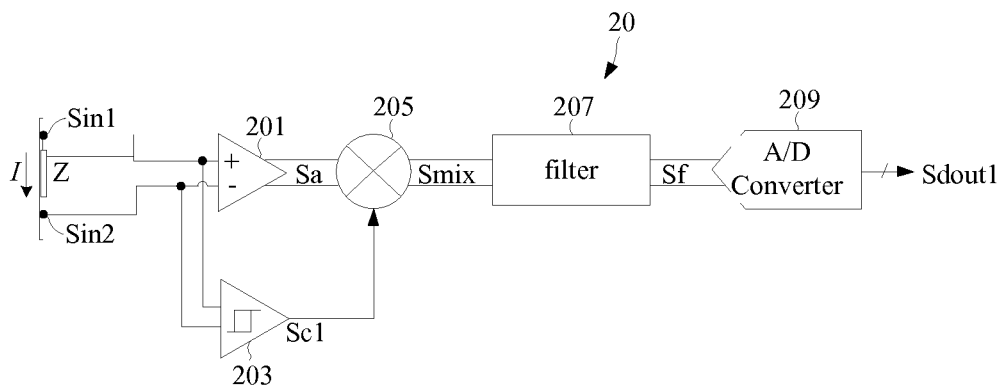
FIG. 2 is a block diagram of one preferred example of the signal process system for a gain detection process according to the invention.

FIG. 2 shows a block diagram of a preferred example of a signal process system 20 according to the invention. Said signal process system 20 is used to detect and process gain (|Z|) part of the sensed sensory signal. As shown in FIG. 2, said signal process system 20 includes at least: a signal amplifier 201, a comparator 203, a mixer 205, a filter 207, and an analog-to-digit converter 209.

As shown in the figure, a current I flows through an impedance Z, and generates the first input signal Sin1 and the second input signal Sin2 on two ends of said impedance Z. Said signal amplifier 201 and said comparator 203 receive said first input signal Sin1 and said second input signal Sin2, respectively. Said signal amplifier 201 amplifies signal level (voltage/current) difference of said first input signal Sin1 and said second input signal Sin2 with an adjustable gain to generate an amplified signal Sa. It is noted that, in this example, said signal amplifier 201 is a voltage (V/V) amplifier. However, in other examples of the invention, said signal amplifier 201 may be replaced with current (I/I), transconductance (IN) or transimpedance (V/I) amplifier as need.

Said comparator 203 compares signal level magnitudes of said first input signal Sin1 and said second input signal Sin2, and generates a first comparison signal SC1 accordingly. If said first input signal Sin1 is larger than said second input signal Sin2, then said first comparison signal SC1 may be a positive saturated output signal (for example, logic 1 output signal); if said first input signal Sin1 is smaller than said second input signal Sin2, then said first comparison signal SC1 is a negative saturated output signal (for example, logic 0 output signal). For example, said comparator 203 may be replaced with a transistor amplifier or comparator capable of generating a logic 1 or 0 output signal (digital circuit) or generating a saturated output signal (analog circuit) as the signal level difference between two input signals is larger than a predetermined threshold.

Said mixer 205 mixes said amplified signal Sa and said first comparison signal SC1 to generate a mixed output signal Smix. For example, said amplified signal Sa and said first comparison signal SC1 may have the same or different frequency components. Said mixer 205 performs frequency mixing process for said amplified signal Sa and said first comparison signal SC1.

Said filter 207 is a low pass filter used for filtering said mixed output signal Smix to filter out signal components not in low frequency in order to generate a filtered output signal Sf with a selected frequency (for example, reserve low frequency signal). In other examples of the invention, said filter 207 is not limited to low pass filter.

Said analog-to-digit converter 209 is used to convert said filtered output signal Sf with the selected frequency into a first digital output signal Sdout1 related to a signal strength. For example, according to said filtered output signal Sf with the selected frequency, said analog-to-digit converter 209 may be a selected other analog-to-digit converter with higher resolution or faster speed.

Figure 3:
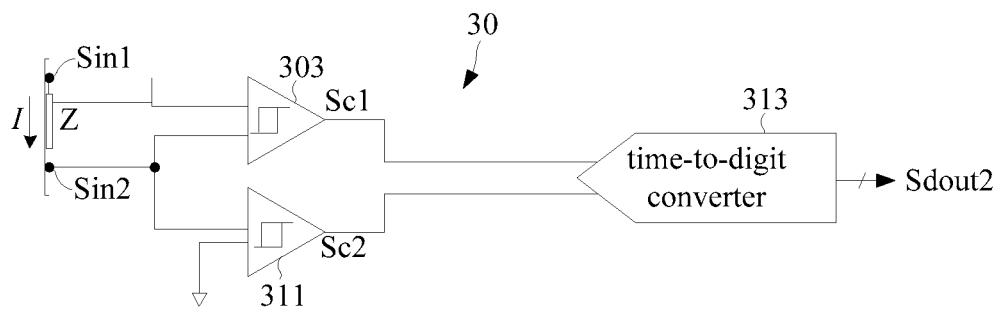
FIG. 3 is a block diagram of one preferred example of the signal process system for a phase detection process according to the invention.

FIG. 3 shows a block diagram of a preferred example of a signal process system 30 according to the invention. Said signal process system 30 is used to detect the phase ($\Phi$) part of a sensed sensory signal. As shown in the figure, said signal process system 30 includes at least: a first comparator 303, a second comparator 311 and a TDC (time-to-digit converter) 313.

As shown in the figure, a current I flows through an impedance Z, and generates the first input signal Sin1 and the second input signal Sin2 on two ends of said impedance Z. Said first comparator 303 and said second comparator 311 receive said first input signal Sin1 and said second input signal Sin2, respectively. Said first comparator 303 compares signal level magnitudes of said first input signal Sin1 and said second input signal Sin2, and generates a first comparison signal SC1 accordingly. If said first input signal Sin1 is larger than said second input signal Sin2, then said first comparison signal SC1 may be a positive saturated output signal (for example, logic 1 output signal); if said first input signal Sin1 is smaller than said second input signal Sin2, then said first comparison signal SC1 is a negative saturated output signal (for example, logic 0 output signal).

Similarly, said second comparator 311 compares signal level magnitudes of said first input signal Sin2 and a reference signal Sref, and generates a second comparison signal SC2 accordingly. If said second input signal Sin2 is larger than said reference signal Sref, then said second comparison signal SC2 is a positive saturated output signal (for example, logic 1 output signal); if said second input signal Sin2 is smaller than said reference signal Sref, then said second comparison signal SC2 is a negative saturated output signal (for example, logic 0 output signal).

For example, in other examples of the invention, said first comparator 303 and said second comparator 311 may be replaced with other appropriate transistor amplifiers or comparators.

Said time-to-digit converter 313 receives said first comparison signal SC1 and said second comparison signal SC2, and may convert a time difference between a rising edge of said first comparison signal SC1 and a rising edge of said second comparison signal SC2 into a second digital output signal Sdout2, or convert a time difference between a falling edge of said first comparison signal SC1 and a falling edge of said second comparison signal SC2 into a second digital output signal Sdout2 related to a phase. For example, depending on design, said time-to-digit converter 313 may also be implemented using simple logic gate combinational circuits or timing circuits.

From the contents shown in both FIG. 2 and FIG. 3, for the member for processing phase signal detection shown in FIG. 3, the adopted technology retrieves and converts signals of the biological tissue to be measured into square wave signals through two comparators (303 and 311) for output, wherein the first comparator 303 may be used with the comparator 203 shown in FIG. 2 simultaneously, followed by making the respective square wave signals (SC1 and SC2) output from the two comparators (303 and 311) to be the input signal of the time-to-digit converter 313. Because there is a certain phase difference between the two signals (SC1 and SC2), that is, there is a certain time difference with respect to time, the characteristic of the time-to-digit converter 313 itself can be used to quantify and convert the time difference between the two signals (SC1 and SC2) into the second digital output signal Sdout2 for output, while said second digital output signal Sdout2 is the signal of the phase part ($\Phi$) generated through the biological tissue to be measured.

Therefore, the signal process system of the invention figures out the inconvenience and shortages of existing impedance detection technologies, such as, for example, incapability of monitoring with the change of biological impedance, larger hardware need, accuracy of generated reference signal, match between reference signals, implementation complexity and power consumption etc.; and may generate physiological parameters with more accuracy and higher reference values in order for evaluation and diagnosis for different syndromes.

Figure 4:
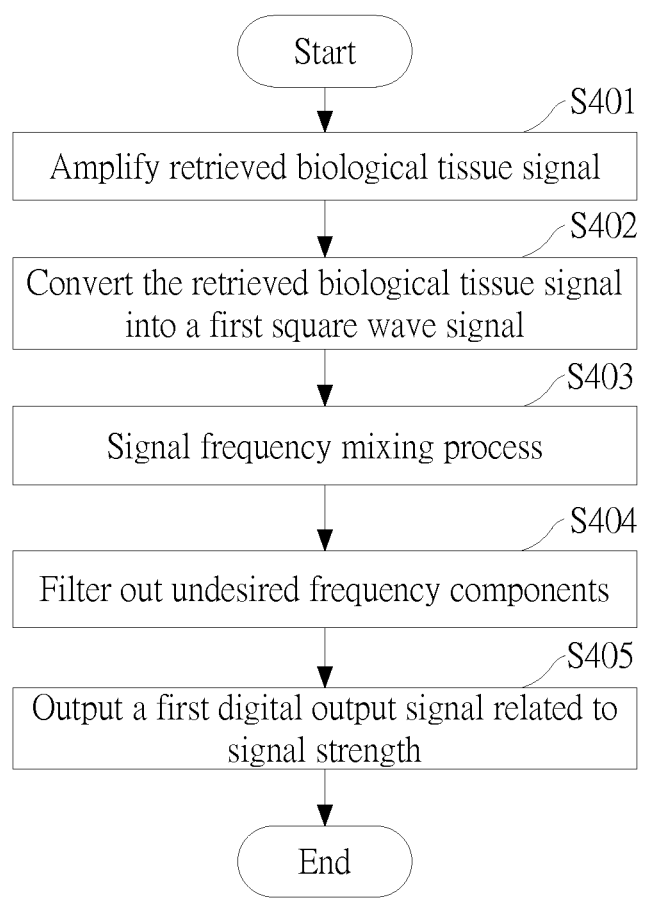
FIG. 4 is a flowchart of one example of the signal process method according to the invention.

FIG. 4 shows a flowchart of one example of the signal process method according to the invention used to illustrate the detection process steps for gain (|Z|) part of the sensed sensory signal. In step S401, the signal level difference of a first input signal and a second input signal is amplified by an adjustable gain to generate an amplified signal. This process step is used to amplify the retrieved biological tissue signal to be measured (i.e., the aforementioned sensory signal), followed by proceeding to step S402. Step S401 may be implemented by means of, for example, a signal amplifier.

In step S402, the signal level magnitudes of said first and second input signals are determined to generate a first square wave signal. This process step is used to convert the amplified biological tissue signal into the first square wave signal, followed by proceeding to step S403. Step S402 may be implemented by, for example, a comparator.

In step S403, a mixed output signal is generated by mixing said amplified signal and said first square wave signal, followed by proceeding to step S404. Step S403 may be implemented by, for example, a mixer (or frequency mixer).

In step S404, said mixed output signal is filtered for filtering out undesired frequency components from said mixed output signal to generate a filtered output signal with a selected frequency, said filtered output signal being used as a gain signal, followed by proceeding to step S405. Step S404 may be implemented by, for example, a filter.

In step S405, said mixed output signal with the selected frequency is converted into a first digital output signal related to a signal strength, which is the gain (|Z|) part of the biological impedance detection, followed by ending the flow. Step S405 may be implemented by, for example, an analog-to-digit converter.

Figure 5:
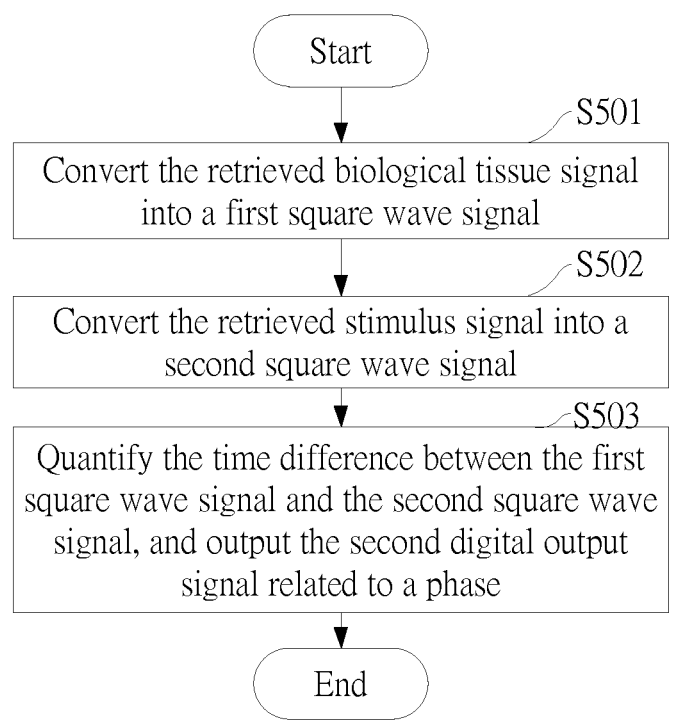
FIG. 5 is a flowchart of another example of the signal process method according to the invention.

FIG. 5 shows a flowchart of another example of the signal process method according to the invention, which is used to illustrate the detection process step for the phase (Φ) part of the sensed sensory signal. In step S501, a first square wave signal is generated by determining the signal level magnitude of said first and second input signals. This process step converts the retrieved biological tissue signal (sensory signal) into the first square wave signal, followed by proceeding to step S502. Step S501 may be implemented by, for example, a comparator. It is noted additionally that the retrieved biological tissue signal disclosed in this step may come from the first square wave signal mentioned in step S402 illustrated in FIG. 4.

In step S502, a second square wave signal is generated by determining the signal level magnitudes of said second input signal and a first reference signals, followed by proceeding to step S503. Step S502 may be implemented by, for example, a comparator. It is noted additionally that this process step converts the stimulus signal that can actuate said biological tissue to be measured to generate the sensory signal into the second square wave signal, that is, to convert the stimulus signal generated by the micro stimulus generator into the square wave signal.

In step S503, the time difference between a rising edge of said first square wave signal and a rising edge of said second square wave signal or the time difference between a falling edge of said first square wave signal and a falling edge of said second square wave signal are converted into a second digital output signal. This process step is used to quantify the time difference of the first square wave signal and the second square wave signal, and output the second digital output signal related to a phase, followed by ending the flow. Step S503 may be implemented by, for example, a time-to-digit converter.

Therefore, the signal process method according to the invention utilizes gain phase detection technology to obtain the physiological property of a biological tissue to be measured, such as biological impedance information. The detection method is according to equation (1).

$$Z=|Z|e^{-j\Phi}=|Z|\cos\Phi - j|Z|\sin\Phi \quad \text{equation (1)}$$

The biological impedance information (Z) is divided into two parts of signals, gain (|Z|) and phase (Φ), for detection, followed by restoring complete impedance information using the detected respective information or through signal process for evaluation and diagnosis of different syndromes.

It is known that the impedance information of the aforementioned biological tissue to be measured may be represented by a real part (Re(Z)) and an imaginary part (Im(Z)), so that the equivalent circuit of said impedance information may be composed of a base resistor (Rb) and parallel connected resistor (R) and capacitor (C) connected in series. Because the stimulus signal source are mainly divided into two forms, sinusoidal wave signal and square wave signal, the equivalent circuit expression of said impedance information would be modified appropriately with different forms of stimulus signal sources. For ease of illustration, a sinusoidal wave signal is used as the stimulus signal source in the invention, for example, and the expression for the impedance information of said biological tissue is as shown in equation (2).

$$Z = |Z|e^{-j\theta} = |Z|\cos\theta - j|Z|\sin\theta$$
$$= \text{Re}(Z) - j\,\text{Im}(Z)$$
$$= R_b + \frac{R}{1+(\omega RC)^2} - j\frac{\omega R^2 C}{1+(\omega RC)^2} \quad \text{equation (2)}$$

As the angular frequency (ω) approaches to infinity in equation (2), the information of a base resistor (Rb) may be obtained, as shown in equation (3).

$$Z_\infty = R_b = |Z|_{\omega \to \infty} \quad \text{equation (3)}$$

Moreover, ωRC in equation (2) is assumed as a constant A, and said constant A may be represented as shown in equation (4).

$$A = \omega RC \quad \text{equation (4)}$$

Equation (4) is substituted according to equation (2) and can be represented as shown in equation (5).

$$A = \frac{\text{Im}(Z)}{\text{Re}(Z) - R_b} = \frac{|Z|\sin\theta}{|Z|\cos\theta - R_b} \quad \text{equation (5)}$$

Equation (5) is substituted into equation (2) to obtain the real part (Re(Z)) in said biological impedance, which can be represented as shown in equation (6); moreover, it can be converted to obtain a parallel resistance (R) according to equation (7).

$$\text{Re}(Z) = R_b + \frac{R}{1+A^2} \quad \text{equation (6)}$$

$$R = (1+A^2)[\text{Re}(Z) - R_b] \quad \text{equation (7)}$$
$$= (1+A^2)(|Z|\cos\theta - Z_\infty)$$

Furthermore, the known base resistor (Rb) and the constant A obtained from calculation are substituted into equation (4), into which magnitude of the angular frequency is further substituted, to obtain a parallel capacitance (C) parameter value, as shown in equation (8).

$$C = \frac{A}{\omega R} \quad \text{equation (8)}$$

Both gain (|Z|) and phase (Φ) information of the detected biological impedance (Z) undergo signal process to restore the parameter values (Rb, R, C) of each element composing the equivalent circuit for the impedance information of said biological tissue, such that said equivalent circuit parameter model representative of said impedance information is built for researches of clinical medicine or biomedicine engineering, but the invention is not limited thereto.

It is noted that, based on the contents of flowcharts contained in FIG. 4 and FIG. 5, those with ordinary knowledge in the art should understand clearly that the steps in each of the flowcharts may be implemented in combination or simultaneously.

Figure 6:
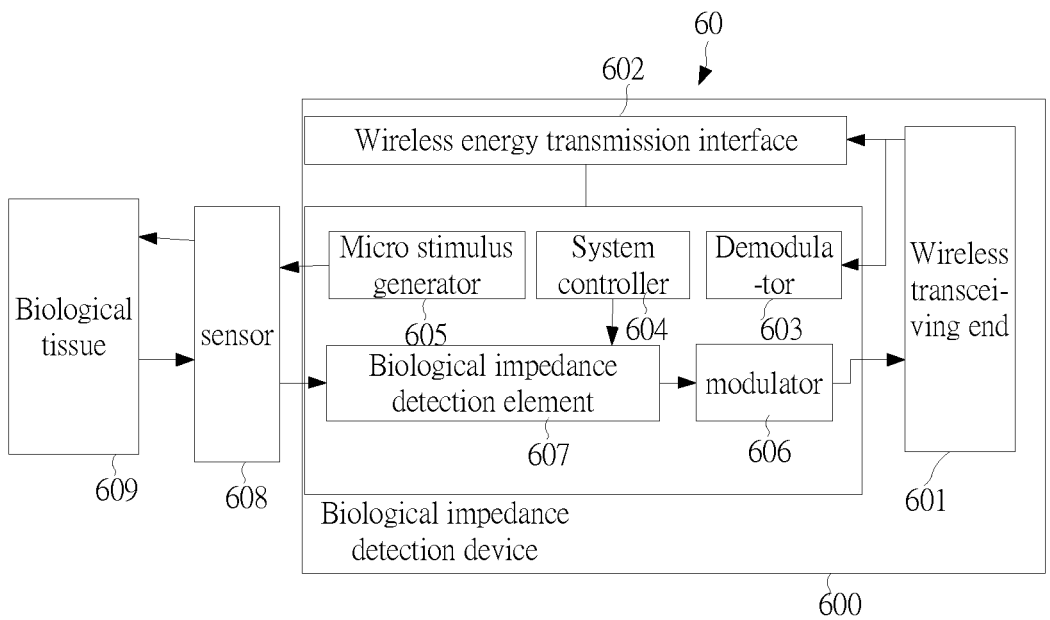
FIG. 6 is an architecture schematic of the biological impedance detection device according to the invention.

FIG. 6 shows an exemplary example of a biological impedance detection system 60 according to the invention. As shown in the figure, said biological impedance detection system 60 includes a biological impedance detection device 600, a sensor 608 and a biological tissue to be measured 609. Said biological impedance detection device 600 includes at least: a wireless transceiving end 601, a wireless energy transfer interface 602, a demodulator 603, a system controller 604, a micro stimulus generator 605, a modulator 606 and a biological impedance detection element 607.

The biological impedance detection device 600 may be a near-body end device that may be implanted in the biological tissue to be measured 609 or carried by the home end of the biological tissue to be measured 609, even a near-end device (not shown in the figure) that may be monitored by doctors or nurse personnel. The near-end device and the near-body end device transmit energy, data and control signals in a wireless coupling manner, followed by generating operating voltage needed by entire chip system through the wireless energy transfer interface of the near-body end device, and the system controller 604 controls stimulus and detection. As such, doctors or nurse personnel may analyze the biological impedance signal on the examination sites of examinees detected by said near-body end device through the near-end device to obtain impedance information of said biological tissue to be measured and create the equivalent circuit parameter model representative of said impedance information. Said sensor 608 obtains the biological impedance signal of the biological tissue to be measured 609 via measurement, and transmits the detected biological impedance signal to the biological impedance detection device 600 for performing the step process illustrated in the aforementioned FIG. 4 and FIG. 5. Said sensor may vary depending on the site to be detected, such as body-surface recording electrode placed on body surface, internal electrode placed inside body, electrode arrays and microelectrode used to observe related property on surface of cell layer, but not limited thereto.

Said wireless transceiving end 601, wireless energy transfer interface 602, demodulator 603, system controller 604 and modulator 606 are used for signal transmission, and the arrangement is not limited to be within said biological impedance detection device 600. Said micro stimulus generator 605 is used for providing stimulus signal to said biological tissue to be measured 609, and the arrangement is not limited to be within said biological impedance detection device 600. Said biological impedance detection element 607 is a signal process system contained in the example illustrated in FIG. 1. It may perform signal process corresponding to the impedance signal obtained by said sensor 608 via measurement to obtain complete impedance information of said biological tissue to be measured 609 via derivation. In addition, it is noted particularly that, from FIG. 2 and FIG. 3, the comparator (or square wave generator) of the biological impedance detection element 607 in the invention for converting sensory signal of the biological tissue to be measured into square wave signal with respect to detection of gain signal and detection of phase signal may be shared. Therefore, hardware requirement and cost may be reduced.

Said wireless transceiving end 601 receives a signal sent by a near-end wireless transceiver of the near-end device monitored by doctors or nurse personnel. The signal is converted into energy through the wireless energy transfer interface 602 to provide operating voltage necessary for demodulator 603, system controller 604, micro stimulus generator 605, modulator 606 and biological impedance detection element 607. For the signal received by the wireless transceiver 601 in said biological impedance detection device 600, another path is demodulated to be a control signal via the demodulator 603 to be transmitted to the system controller 604 for controlling stimulus waveform frequency, amplitude magnitude generated for the micro stimulus generator 605 and controlling the biological impedance detection element 607; said demodulator 603 and modulator 606 essentially, respectively, demodulate the received signal sent from the near-end device monitored by doctors or nurse personnel or modulate the detection signal desired to be transmitted. This is helpful to eliminate or mitigate problems, such as degradation, interference or the like, of signal in transmission channel.

Doctors or nurse personnel may modify stimulus parameters desired to be set through user interface (not shown in figure) provided by said near-end device as they regard that the mechanism of the biological impedance detection device 600 has to be adjusted. Moreover, it is transmitted to the wireless transceiving end 601 of said biological impedance detection device 600 through signal control and process system and the wireless transceiver provided by said near-end device. Thereby, for example, modification of stimulus parameters or control of signal output format is performed to achieve the goals of adjusting gain phase detection parameters appropriately for biological impedance detection and physiological monitoring.

The invention may be applied to cancer cell detection. The biological impedance detection device 600 shown in FIG. 6 may be made in module or chip form to be implanted to the biological tissue to be measured (monitoring site after cancer surgery). Doctors or nurse personnel monitor or operate signal, which carries control instruction, through near-end device to request the biological impedance detection device 600 to perform stimulus and detection actions, and to return the signal carrying biological impedance to the near-end device. Computation analysis and display are performed according to the returned biological impedance information to implement the system that can complete biological impedance detection process in an implantable or portable manner.

The examples above are only illustrative to explain principles and effects of the invention, but not to limit the invention. It will be apparent to those skilled in the art that modifications and variations can be made without departing from the spirit and scope of the invention. Therefore, the protection range of the rights of the invention should be as defined by the appended claims.

What is claimed is:

1. A biological impedance detection device for a near-end device that is monitored by doctors or nurse personnel to perform signal process using a first digital output signal and a second digital output signal, said biological impedance detection device including:

a micro stimulus generator for providing a stimulus signal to a biological tissue to be measured;

a biological impedance detection element including a gain detection module and a phase detection module;

a wireless transceiving end for receiving a signal from said near-end device or transmitting a local signal to said near-end device;

a system controller used to control said micro stimulus generator and said biological impedance detection element for said near-end device to restore an impedance information of said biological tissue to be measured from said first digital output signal and said second digital output signal, and to create an equivalent circuit parameter model representative of said impedance information;

a demodulator for demodulating a signal from said near-end device;

a modulator for modulating the transmitted local signal; and a wireless energy transfer interface for providing electrical energy to provide the electrical energy necessary for said demodulator, said system controller, said micro stimulus generator, said modulator and said biological impedance detection element.

2. The biological impedance detection device as claim 1, wherein said gain detection module of said biological impedance detection element includes at least:

a signal amplifier for amplifying a sensory signal to generate an amplified signal;

a first square wave generator for converting said sensory signal into a first square wave signal;

a signal mixer, which mixes said amplified signal and said first square wave signal to generate a mixed output signal;

a filter for filtering said mixed output signal to filter out undesired frequency component from said mixed output signal for generation of a filtered output signal with a selected frequency; and an analog-to-digit converter for converting said filtered output signal with the selected frequency into said first digital output signal.

3. The biological impedance detection device as claim 2, wherein said stimulus signal passes through said biological tissue to be measured by injecting a minor AC electrical signal for a sensor to sense the sensory signal of said biological tissue to be measured by means of the principle of Ohm's Law.

4. The biological impedance detection device as claim 2, wherein said phase detection module of said biological impedance detection element includes at least:

a second square wave generator for converting said stimulus signal into a second square wave signal; and a time-to-digit converter for quantifying a time difference between said first square wave signal and said second square wave signal to output said second digital output signal.

5. The biological impedance detection device as claim 1 being implanted into said biological tissue to be measured in a chip form.

6. The biological impedance detection device as claim 1, wherein the equivalent circuit parameter model representative of said impedance information is formed by connecting a base resistor and a set of parallel connected resistor and capacitor in series.

* * * * *